(12) United States Patent
Dumais et al.

(10) Patent No.: US 7,471,866 B2
(45) Date of Patent: Dec. 30, 2008

(54) WAVEGUIDING STRUCTURES WITH EMBEDDED MICROCHANNELS AND METHOD FOR FABRICATION THEREOF

(75) Inventors: Patrick Dumais, Ottawa (CA); Chris Ledderhof, Richmond (CA); Claire Callender, Nepean (CA); Chantal Blanchetiere, Ottawa (CA); Julian Noad, Carp (CA); Glendon Lovell, Nepean (CA)

(73) Assignee: Her Majesty the Queen in Right of Canada as Represented by the Minister of Industry, Through the Communications Research Centre Canada, Ottawa (CA)

( * ) Notice: Subject to any disclaimer, the term of this patent is extended or adjusted under 35 U.S.C. 154(b) by 362 days.

(21) Appl. No.: 11/167,229

(22) Filed: Jun. 28, 2005

(65) Prior Publication Data
US 2005/0287696 A1 Dec. 29, 2005

Related U.S. Application Data

(60) Provisional application No. 60/583,365, filed on Jun. 29, 2004.

(51) Int. Cl.
*G02B 6/10* (2006.01)
*H01L 21/00* (2006.01)

(52) U.S. Cl. .................... 385/132; 385/129; 438/27; 438/29; 438/31; 438/65; 438/69

(58) Field of Classification Search .............. 438/27, 438/29, 31, 65, 69; 385/129–132
See application file for complete search history.

(56) References Cited

U.S. PATENT DOCUMENTS

| 5,166,101 | A | 11/1992 | Lee et al. | |
| 5,562,838 | A * | 10/1996 | Wojnarowski et al. | 216/24 |
| 5,719,084 | A | 2/1998 | Mallon et al. | |
| 6,246,825 | B1 * | 6/2001 | Kershaw | 385/132 |
| 2003/0180024 | A1 * | 9/2003 | Edlinger et al. | 385/132 |

OTHER PUBLICATIONS

"A prealigned process of integrating optical waveguides with microfluidic devices", Lien et al, IEEE Phot. Tech. Let. vol. 16, No. 6, 2004.

(Continued)

*Primary Examiner*—Frank G Font
*Assistant Examiner*—Charlie Peng
(74) *Attorney, Agent, or Firm*—Teitelbaum & MacLean; Neil Teitelbaum; Doug MacLean (57) ABSTRACT

The invention provides a method for fabricating planar waveguiding structures with embedded microchannels. The method includes the step of depositing, over a planar template having at least one indented feature comprising a ridge of a first optical material and a narrow trench adjacent thereto, a second optical material, and the step of subsequent annealing thereof, so that an embedded hollow microchannel forms within the trench. The method provides planar structures wherein the ridge and the embedded microchannel cooperate to form an optical waveguiding structure having a waveguiding direction collinear with the embedded microchannel. Embodiments of the method for forming microfluidic devices integrating ridge waveguides with hollow microchannels having surface access points for fluid delivery, and for forming photonic crystals, are disclosed together with corresponding device embodiments.

21 Claims, 9 Drawing Sheets

OTHER PUBLICATIONS

"Silica-on-Silicon Optical Sensor Based on Integrated Waveguides and Microchannels", Phot. Tech. Lett. No. 17(2), pp. 441-443, 2005.
"Microchannels for the Integration of Liquid Media in Silica Waveguide Structures" Technical Digest of Int. Photonics Research and Applications, Paper IMD3, San Diego, CA Apr. 11-13, 2005.
"Fabrication of Microchannels Integrated with Silica Waveguides", Technical Digest of Integrated Photonics Research and Applications, Paper IMD4, San Diego, CA, Apr. 11-13, 2005.

* cited by examiner

WAVEGUIDING STRUCTURES WITH EMBEDDED MICROCHANNELS AND METHOD FOR FABRICATION THEREOF

CROSS-REFERENCE TO RELATED APPLICATIONS

The present invention claims priority from U.S. Provisional Patent Application No. 60/583,365 filed Jun. 29, 2004, entitled "Novel Method for Fabricating Uniform, Micron-Sized, Embedded Arrays of Channels in Silica Glass Layer Structures", which is incorporated herein by reference.

TECHNICAL FIELD

The present invention relates to methods of fabricating planar waveguiding structures with integrated embedded microchannels and microchannel arrays, and to optical devices incorporating microfluidic channels coupled to optical waveguides.

BACKGROUND OF THE INVENTION

Optical waveguiding structures incorporating embedded hollow microchannels and microchannel arrays are used in a variety of applications, ranging from waveguides in three-dimensional (3D) and two-dimensional (2D) photonic band-gap materials, or photonic crystals, to microfluidic systems for optical detecting and testing microscopic quantities of organic and non-organic molecules in liquids, for monitoring biochemical reactions, for use in lab-on-a-chip devices and chemical and environmental sensors. Integrated systems including microfluidic channels and optical waveguides can also be of interest for optical devices for controlling and generating light, such as lasers, optical modulators, switches etc.

Photonic crystals are artificially structured materials consisting of 3D or 2D periodic structures with typical periods ranging from about a micron down to hundreds of nanometers, which give rise to photonic band gaps affecting propagation of light similarly to the way periodic potentials in semiconductor or dielectric crystals affect the motion of electrons by defining allowed and forbidden electronic energy bands. Photonic bandgap materials can enable a range of novel optical devices and functions such as low-loss waveguiding in sharp waveguide bends, high-reflectivity omnidirectional mirrors and inhibition of spontaneous emission.

Fabrication of photonic band gap structures in silicon-compatible material systems is of especial interest for many applications because it enables an easy integration of such structures with conventional, such a silica-on-silicon planar waveguides. Such fabrication typically requires a tightly controlled 2D and 3D patterning processes for creating 2D or 3D arrays of voids in the material. While for obtaining a true photonic crystal, wherein light propagation is prohibited in all three dimensions for certain wavelengths, fabrication of true 3D arrays of micro-voids is generally required, such fabrication can be prohibitively expensive. Fortunately, for many applications having 2D or even 1D arrays of microchannels embedded in an optical material, or even individual embedded microchannels coupled to optical waveguiding structures, can be sufficient.

In planar silicon-based materials, 2D photonic crystals have typically been fabricated by forming microchannel arrays wherein the microchannels are oriented in vertical direction relative to the structure, i.e. normally to its main planar surface. Planar waveguides can be formed in such structures by forming an optical path in the structure wherein the microchannels are absent, so to guide light in a direction normal to the microchannels surrounding the waveguide. On the other hand, photonic band gap optical fibers, also known as "holey" optical fibers, have hollow micro-channels which are oriented along the waveguiding direction of the finer, generally parallel to the fiber's core. In holey fibers, such orientation of the voids enables a range of useful optical functions, including single mode operation over a wide wavelength range, polarization control, dispersion compensation, transmission of high optical power etc. However, to the best of the inventor's knowledge, no planar waveguiding structures with photonic band gaps have been disclosed wherein the microchannels are oriented in-plane with the substrate, along the waveguiding direction.

Planar structures integrating optical waveguides and enclosed microchannels oriented in-plane with a substrate are known in microfluidic applications, e.g. for optical probing of microscopic amounts of fluids delivered into the microchannels. Such integrated waveguide-microchannel structures can enable also incorporation of active materials into silicon or silica-based materials for fabrication of active photonic devices such as optical modulators, switches, lasers and amplifiers. Various method for fabricating such microchannels for microfluidic devices have been disclosed in the art, including methods that enable their incorporation in planar silicon structures with optical waveguides. These prior art methods typically include formation of open microchannels in a surface layer of a silicon-based planar structure, and a step of bonding a cover plate onto said surface to form one or more enclosed microchannels from the open microchannels. The enclosed microchannels formed this way are typically oriented to cross a waveguide, so to create one or more intersection points wherein a waveguiding mode interacts with a fluid within the enclosed microchannel. U.S. Pat. No. 6,438,279, issued to Craighead, et al., discloses such fabrication techniques for forming microcapiliary and waveguide structures.

However, these prior-art method for formation of enclosed microchannels crossing waveguides have several drawbacks. The additional step of bonding or gluing a top cover plate technique is outside of common commercial techniques of silicon processing, and complicates the fabrication process. Microchannel structures fabricated using this process are limited to a single layer. The microchannels are typically located at the surface, are difficult to seal and fragile. The use of single-point liquid-optical field interaction, wherein the fluid interacts with an optical mode only in points of microchannel-waveguide interactions, greatly limits the interaction length and thus reduces beneficial effects of such interactions. Also, the cover-plate techniques typically provide microchannels which have substantially trapezoidal or rectangular cross-sections with shapes which are difficult to control.

It would therefore be advantageous to have a method of fabricating integrated microchannel-waveguide structures using only conventional techniques of silicon processing, such as photolithographic patterning, etching and silica deposition, which does not use the cover-plate bonding step, enables tightly controlled co-fabrication of embedded microchannels and waveguides in co-linear orientation for increasing the useful fluid-optical mode interaction length, wherein the microchannels and waveguides are co-fabricated controllably close to each other to enable their optical coupling through evanescent field interaction. It would also be advantageous if the same method would enable fabrication of 1D and 2D arrays of microchannels having substantially circular or elliptical cross-sections with tightly controlled parameters, e.g. for applications wherein optical waveguides are integrated with photonic band-gap structures.

An object of the present invention is to provide a method for controlled fabrication of planar waveguiding structures with embedded microchannels having substantially circular or elliptical cross-sections in silicon-based glass materials.

Another object of the present invention is to provide a method for fabricating waveguiding structures comprising uniform 1D and 2D arrays of embedded microchannels with controlled microchannel parameters.

Another object of the present invention is to provide a method for fabricating monolithic waveguiding structures comprising embedded microchannels in close proximity to ridge waveguides, wherein the ridge waveguides and the embedded microchannels are fabricated in parallel using a same technological process.

Another object of the present invention is to provide a simplified method of fabrication of coupled waveguide-microchannel structures for microfluidic applications without using the cover plate bonding or gluing step for enclosing the microchannels.

SUMMARY OF THE INVENTION

In accordance with the invention, a method for fabricating an optical waveguiding structure comprising embedded microchannels is provided. The method comprises the steps of: a) forming an indented feature on a planar substrate by forming a first ridge with a trench adjacent thereto with a first optical material, b) depositing a second optical material over the indented feature so that at least a partially capped channel is formed from at least a portion of the trench, and c) reflowing the second optical material by thermal annealing to form an embedded microchannel from said at least partially capped channel; wherein the first ridge and the embedded microchannel cooperate to form the optical waveguiding structure having a waveguiding direction collinear with the embedded microchannel.

In accordance with another aspect of this invention, the step (a) of the method comprises forming the trench with a widened portion at one end thereof, so that in step (c) an inlet for the embedded microchannel forms from said widened portion, said inlet having an opening in an upper surface of the second optical material for providing an in-plane access to the embedded microchannel.

Another aspect of the present invention relates to using the method provided in the present invention for forming microfluidic devices integrating waveguides and the embedded microchannels. In one embodiment related to this aspect of the invention, step (a) comprises forming the trench between the first ridge and a second ridge of the first optical material, forming a third ridge adjacent to the first ridge and separated therefrom by a second trench, and wherein step (c) comprises forming a three-core optical coupler having two coupling regions optically coupling adjacent cores of the three-core coupler, the coupling regions comprising embedded microchannels, the method further comprising: delivering a fluid into at least one of the microchannels, coupling a laser beam into one of the cores at one end of the three-core optical coupler, and optically sampling the fluid using a sensing device coupled to one of the cores at the other end of said coupler.

Another feature of the present invention provides a microchannel-waveguide junction device, comprising: a microchannel having a portion embedded in an optical material disposed over a substrate, said embedded portion aligned along an optical path; a ridge waveguide having an end portion aligned with the embedded portion of the microchannel along the optical path for coupling light into the embedded portion of the microchannel; and, means for delivering sample material into the embedded portion of the microchannel for affecting a characteristic of the light coupled into the embedded portion of the microchannel.

In another aspect, the method of the present invention adopted for forming microchannel arrays and photonic crystal structures is provided, wherein step (a) of the method comprises forming a plurality of trenches, so that a plurality of embedded microchannels is formed in step (c), the method further comprising repeating steps (a)-(c) to form a waveguiding structure comprising a two-dimensional array of embedded microchannels, wherein said two-dimensional array of embedded microchannels is dimensioned to form a photonic crystal.

BRIEF DESCRIPTION OF THE DRAWINGS

The invention will be described in greater detail with reference to the accompanying drawings which represent preferred embodiments thereof, wherein:

FIGS. 1A-1F is a set of diagrams illustrating fabrication steps of a waveguiding structure according to the method of the present invention, wherein:

DETAILED DESCRIPTION

First, the method of the present invention for fabricating waveguiding structures with microchannels embedded therein will now be described with reference to FIGS. 1A-1F, illustrating main steps of the method in one exemplary embodiment thereof.

Figure 1A:
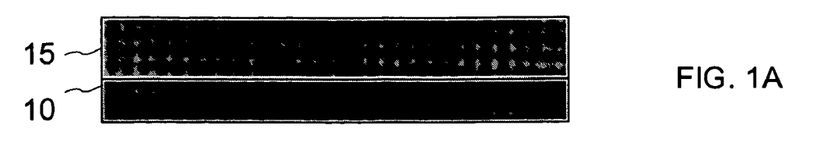
FIG. 1A is a diagram showing a planar substrate with a layer of first optical material deposited thereon.

In this embodiment, the method starts with depositing a layer 15 of a first optical material on a planar substrate 10, resulting in a planar structure shown in FIG. 1A. The planar substrate 10 is preferably a silicon substrate, but can be also any other substrate, for example made of any other semiconductor or dielectric material, such as glass, or a ceramic, on which the optical material 15 can be deposited to form a monolithic structure.

In the context of this specification, the term "planar", used in relation to a substrate, means that a relevant portion of said substrate has a main surface and a radius of curvature thereof substantially exceeding dimensions of geometrical features of the present invention formed over said substrate. The term "planar" used in relation to waveguiding and other structures of the present invention means that said structures are formed on a planar substrate.

The term "optical material" is used herein to mean a material which is substantially transparent for optical radiation at an operating wavelength λ of the waveguiding structures of the present invention, which typically lies between about 2.0 um and about 0.3 um, depending on the application. The first optical material can be silicon, silica, doped silica, or other suitable material, or can be formed by a combination of several suitable materials, e.g. in a layered structure. In a preferred embodiment, the first optical material 15 is a high melting temperature silica-based glass, e.g. a germanium-doped silica, deposited on the substrate 10 by plasma-enhanced chemical vapor deposition (PECVD). In a following optional step, the layer 15 is annealed at a high temperature to densify and optimize the optical quality of the glass as known in the art.

The substrate 10 can include one or more layers formed therein or thereupon, as known in fabrication of planar waveguides, for example for providing an improved bonding of the first optical material 15 thereto, or for providing a lower cladding layer for the waveguiding structure which is to be formed on the substrate 10 as described hereinbelow. In some embodiments, the substrate 10 includes an upper layer of thermal silicon oxide for providing a lower cladding for the waveguiding structures of the present invention.

Figure 1B:
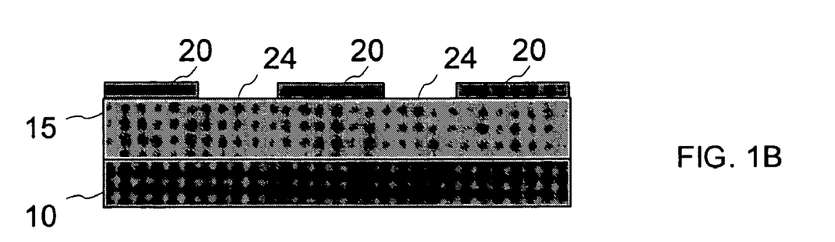
FIG. 1B is a diagram of the structure shown in FIG. 1A with a mask layer patterned on top of it.
Figure 1C:
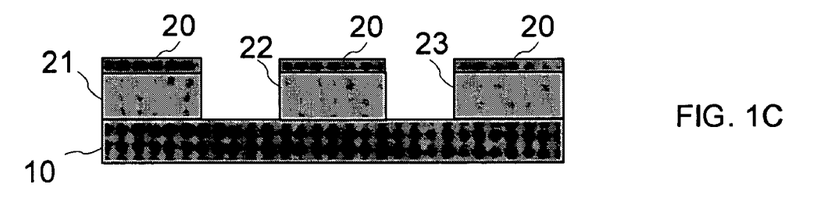
FIG. 1C is a diagram of the structure shown in FIG. 1B after the step of etching of the first optical material.

In a next step, using photolithographic techniques, a mask 20 having open gaps 24 to expose the first optical material 15 is patterned onto an upper surface of the first optical material 15, as shown in FIG. 1B. The mask 20 defines a pattern of waveguiding features to be formed in the first optical material 15. This pattern, in a processing step hereinafter referred to as patterning, is first transferred to the glass layer 15, as shown in FIG. 1C, to a tightly specified depth d by etching the glass 15 in the openings of the mask 20, preferably using one of the dry etching techniques. In a preferred embodiment, the mask 20 is a metal mask, and the patterning of the glass layer 15 is done by a reactive ion etching (RIE), which is a well-known technique. Then, the metal mask 20 is removed, e.g. by dissolving it in a suitable acid solution, as would be known to those skilled in the art. The depth d of the RIE etching depends on a particular choice of the first and a second optical materials as described hereinbelow, on the operating wavelength λ, design characteristics of the waveguiding structure to be formed, and on etching and deposition techniques used in the method, and may vary from one embodiment to the other, but is preferably between 1 μm and 15 μm.

Figure 1D:
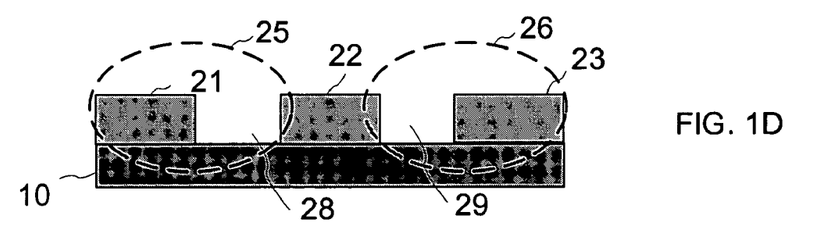
FIG. 1D is a diagram showing a ridge template obtained by removing the mask from the structure shown in FIG. 1C.

Referring now to FIG. 1D, the aforedescribed steps result in forming at least one indented feature 25 on the planar substrate 10, by forming a first ridge 21 and a trench 28 adjacent thereto from the first optical material 15. The indented feature 25 is a basic building block used in the formation of the waveguiding structure according to the present invention. As shown in FIG. 1D and described in detail hereinafter in this specification, more than one indented feature can be simultaneously formed by forming a plurality of ridges with trenches adjacent thereto, the ridges and trenches forming a template for fabricating the waveguiding structure of the present invention. In a typical configuration of the present invention, a trench is positioned between two ridges, as e.g. the trench 28 is positioned between the first ridge 21 and a second ridge 22 formed from the first optical material or other suitable optical material. In other embodiments, a trench can be bounded by a ridge on one side and a stepped feature other than a ridge formed in the first optical material 15. The ridge template shown in FIG. 1D includes the first ridge 21, a second ridge 22 and a third ridge 23, the three ridges defining the first and second trenches 28 and 29, respectively.

Figure 1E:
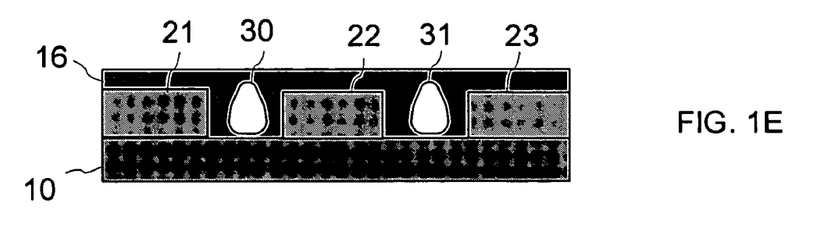
FIG. 1E is a diagram of the structure shown in FIG. 1D after the step of depositing of a second optical material.

Referring now to FIG. 1E, in a next step a layer of a second optical material 16 is deposited over the template including the indented features 25 and 26. The second optical material 16, the deposition method and widths of the trenches 28, 29 are such that the second optical material grows on the template surface in a non-conformal manner, creating triangular-shaped voids, or hollow air channels 30 and 31 from the trenches 28 and 29 between the ridges 21 and 22, and the ridges 22 and 23, respectively, so that the two channels 30 and 31 are at least partially capped by the second optical material 16. The layer 16 of the second optical material will also be referred hereinafter as a capping layer. In the embodiment considered therein, the second optical material 16 is a doped glass, such as e.g. a borophosphosilicate glass (BPSG), having a melting temperature lower than the melting temperature of the first optical material 15, which is deposited using the PECVD method. By way of example, the trenches 28, 29 have a width w between 0.7 μm and 8 μm, and their depth d is between 1 μm and 15 μm, with an aspect ratio d/w preferably about 1.5 or larger.

Figure 1F:
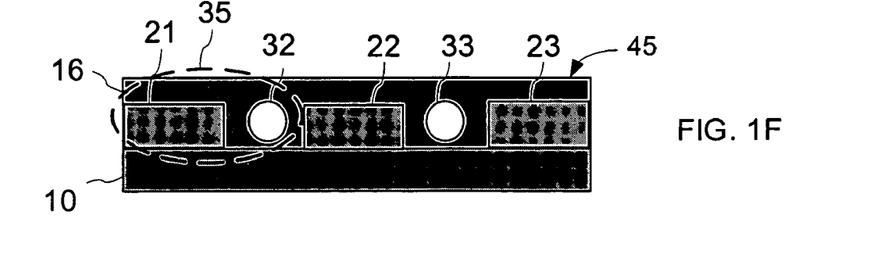
FIG. 1F is a diagram of the waveguiding structure obtained by annealing the structure shown in FIG. 1E.

The structure is then annealed at a high temperature over a period of time sufficient to cause a re-flow of the second optical material and formation of embedded microchannels 32 and 33 shown in FIG. 1F, the embedded microchannels 32 and 33 preferably having an elliptical, and most preferably—a substantially circular cross-section of a pre-defined diameter, but short enough so not to cause closing of the channels. This step results in a planar waveguiding structure incorporating embedded hollow microchannels, and having an upper surface 45.

Figure 2:
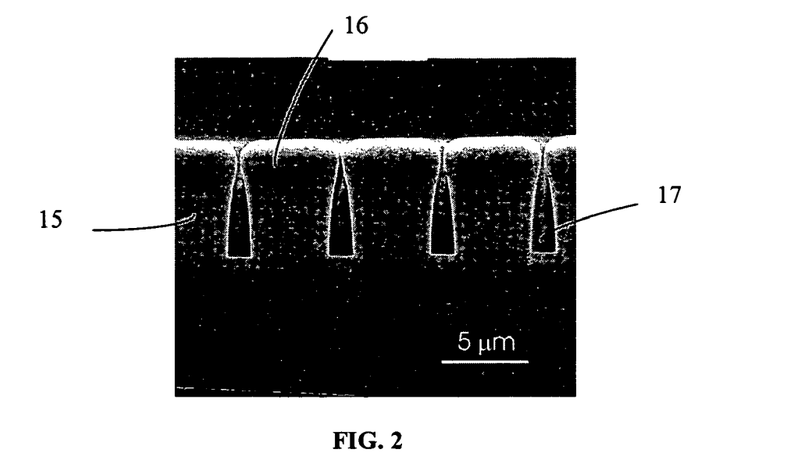
FIG. 2 is a photograph of a ridge template with partially closed microchannels prior to annealing.

By way of example, FIG. 2 shows a photograph of a ridge structure having the layer 16 of BPSG glass deposited over an array of closely-spaced ridges prior to the step of annealing, showing four partially-capped microchannels 17 formed in spacings between the ridges.

Figure 3A:
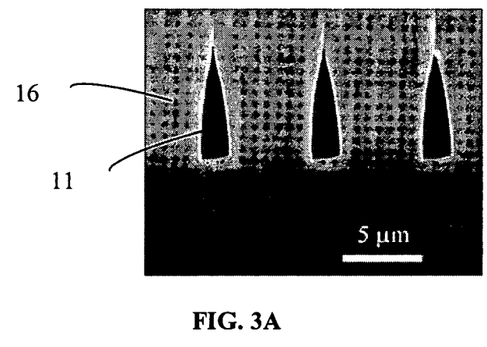
FIG. 3A is a photograph of a ridge template incorporating enclosed microchannels prior to annealing.
Figure 3B:
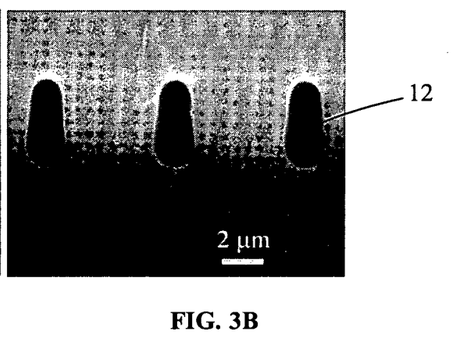
FIG. 3B is a photograph of the ridge template incorporating enclosed microchannels after 4 hours of annealing.
Figure 3C:
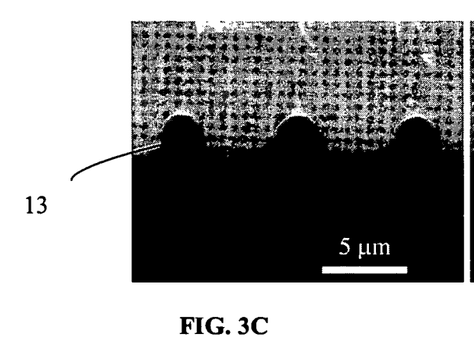
FIG. 3C is a photograph of the ridge template incorporating enclosed microchannels after 8 hours of annealing.
Figure 3D:
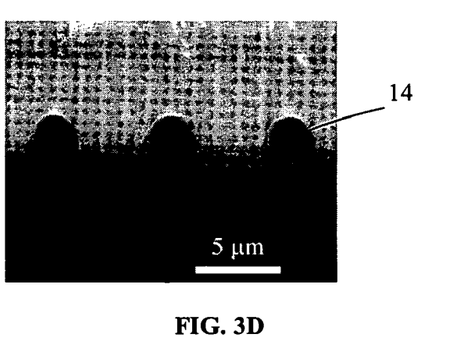
FIG. 3D is a photograph of the ridge template incorporating enclosed microchannels after 12 hours of annealing.

The reshaping of the hollow air channels during the step of annealing is illustrated in FIGS. 3A-D, wherein the channels at different annealing stages are labeled with numerals 11, 12, 13 and 14 respectively. The channel shape starts from its initial triangular shape 11 shown in FIG. 3A, the channels become pear-shaped slots after 4 hours of annealing at 1050 degrees centigrade as shown in FIG. 3B, and finally the channels becomes substantially circular channels 13 after an 8-hour anneal at 1050 C as shown in FIG. 3C. Further annealing diminishes the size of the channels, as shown in FIG. 3C; the channels may disappear altogether for long enough annealing times. The 8-hour anneal is typically sufficient to bring the refractive index of the BPSG to a stable value.

The aforedescribed fabrication steps of depositing and subsequent annealing of the BSPG layer 16 transforms the ridge template shown in FIG. 1D in an optical waveguiding structure, wherein at least one the ridges 21,22, 23 and one of the embedded microchannels 32, 33 adjacent thereto, e.g. the first ridge 21 and the embedded microchannel 32, are closely spaced and dimensioned so to be optically coupled, and cooperate to form an optical waveguiding structure 35 having a waveguiding direction which is normal to the plane of FIG. 1F and collinear with the embedded microchannels. The waveguiding structure 35 is a building block that can be used to form a plurality of functional waveguiding devises of varying complexity, with several exemplary embodiments thereof described hereinafter in this specification.

Note that creating embedded micro-voids in spaces on a substrate between conducting lines by depositing a layer of low-temperature glass such as the BPSG over it, is known in the art of manufacturing electrical integrated circuits (ICs). The BPSG has been used as an insulating layer applied over stepped surfaces of integrated circuits formed on semiconductor wafers because of its relatively low melting temperature, which permits subsequent heating of the layer to flow the glass to thereby planarize the structure.

Micro-voids typically appear in such a layer between closely spaced apart raised lines due to differing rates of the glass deposition on a bottom surface of a narrow trench and on its wall. This void formation in the insulating layer of the integrated circuits is often considered to be a drawback of the process; U.S. Pat. No. 5,166,101 therefore teaches a two step process wherein a composite BPSG insulating and planarizing layer is formed over stepped surfaces of a semiconductor wafer so that formation of discernible voids is avoided.

Others had proposed to make use of the voids, when they appear between closely spaced conductor lines in the BPSG isolating layer of ICs, for reduction of a parasitic capacitance between the conductor lines. For example, U.S. Pat. No. 5,719,084 issued to Mallon et al., which is incorporated herein by reference, discloses a controlled formation of voids in integrated circuit doped glass dielectric films; the voids have a low dielectric constant, thereby reducing the parasitic capacitance between adjacent conductors for increased integrated circuit speed.

Similar to the teachings of Mallon, the present invention makes use of the voids formed in a BPSG layer by controlling their formation. However, the additional functionality and the structural differences provided by the instant invention are significant. The present invention differs from the prior-art by providing the method of fabricating optical waveguiding structures incorporating one or more embedded microchannels as an integral part of said structures, wherein the ridge and the embedded microchannel cooperate to form the optical waveguiding structure having the waveguiding direction collinear with the embedded microchannel. As opposed to a method of Mallon, the formation of the microchannels in the present invention is accomplished not between closely-spaced conductors, but in the absence of conductors between ridges formed of the optical material. The use of a single material system—e.g. silica—in the preferred embodiments of the present invention to form both the template 15 and the void layers 16 means that the waveguiding structure can have tightly controlled properties. This is an advantage over previous methods of fabricating voids in glass using components of CMOS circuitry as templates, since the optical properties of the structures of the present invention can be tailored to optimize waveguiding properties thereof.

As those skilled in the art would appreciate, for the ridges and trenches defined in the present invention to cooperate, being optically coupled, for forming an optical waveguiding structure, they have to satisfy certain dimensional and refractive index criteria that do not apply to the void formation between IC conductors; for example, the ridges and the trenches in the present invention have widths which are in a pre-determined relationship with the operating wavelength $\lambda$, and with at least one of a refractive index $n_1$, of the first optical material, and a refractive index $n_2$ of the second optical material. Particulars of these criteria differ for different embodiments of the optical waveguiding structures formed by the method of the present invention, some of which are described hereinbelow in this specification by way of example, but could be easily construed by those of ordinary skill in the art for each particular embodiment, using known methods and software for designing waveguiding structures.

Several embodiments of the method of the present invention for fabrication of optical waveguiding structures for microfluidic applications, and several novel device structures enabled by the method, will now be described.

Advantageously, the aforedescribed method of the present invention, wherein the ridge waveguides and the embedded parallel microchannels having substantially circular cross-sections are co-fabricated in one relatively simple process using well-established semiconductor and waveguide fabrication technologies, enables integration of liquid media in microscopic amounts into monolithic optical waveguiding structures without the need for the additional step of cover plate bonding to cap the trenches, as commonly used in the art for forming enclosed microchannels. Such integration can be easily accomplished by filling the embedded microchannels with any liquid that can be injected into the channels, e.g. under pressure or, preferably, drawn therein using capillary action. A large range of materials such as organic solvents, polymer solutions, optical epoxies, liquid crystals and quantum dot suspensions can thus be straightforwardly integrated into an optical device without developing specific fabrication processes. The resulting structure can be used for optical testing of microscopic amounts of fluids and for controlling of light using fluidic materials. Devices fabricated using the method of the present invention, wherein the microchannels are fully embedded into the waveguiding structure, are expected to have superior characteristics compared to the prior-art devices fabricated by cover plate bonding, which can be fragile and typically can only have channels near the upper surface of the structure.

As another advantage, the method provides for longitudinal light-liquid interaction due to co-linearity of the microchannels and the direction of the waveguiding, i.e. the light propagation direction. This longitudinal interaction enables a larger light-liquid interaction length, thereby advantageously amplifying useful effects of these interactions compared to the prior-art structures having waveguides intersecting microchannels, as described for example in an article "*A prealigned process of integrating optical waveguides with microfluidic devices*", by V Lien et al., IEEE Phot. Techn. Let. Vol. 16, No. 6, 2004. The microchannel shape, diameter and distance to the adjacent ridge or ridges can be controlled with high precision by varying the process parameters such as the trench width and depths, composition of the first and second optical materials, and the annealing times. By way of example, microchannels having circular cross-sections with specific diameters in the range 2-3 μm can be formed in 3-8 μm wide trenches having the aspect ratio d/w exceeding 1.5, by depositing the second optical material 16 having a reflow temperature of 1050 degrees centigrade, so that the ratio of the thickness of the layer 16 to the trench depth is greater than 1.0, and using the annealing time of at least 8 hours or longer.

Another advantage of the method of the present invention, is that it provides an easy way for forming surface access points to the microchannels, which can be important for microfluidic applications. In the conventional cover-plate bonding techniques, such access points are typically formed by drilling access holes in the top cover plate, requiring an additional fabrication step of precision drilling. In the method of the present invention, the surface access points for the embedded microchannels can be simultaneously formed in the same steps with forming the microchannels themselves, without the need for the additional fabrication step of drilling access holes in the structure.

Figure 4:
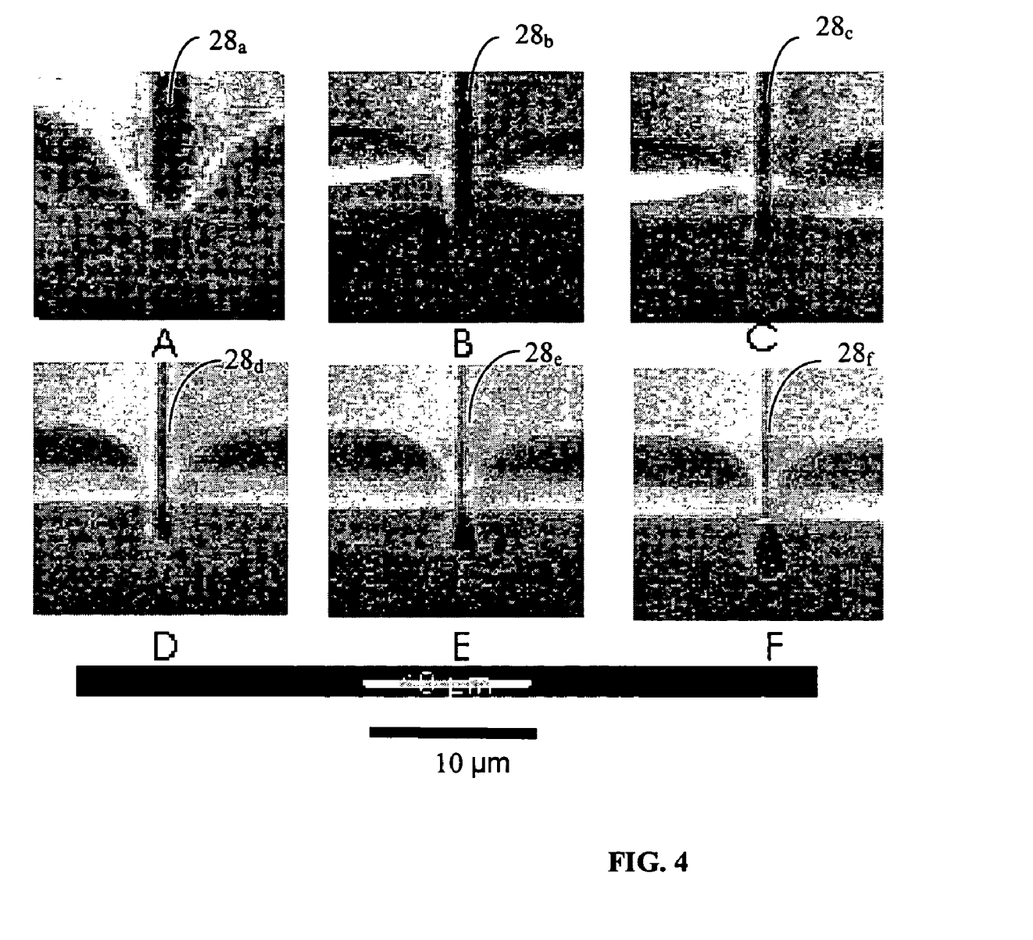
FIG. 4 is a diagram showing 6 microchannels formed inside trenches of varying widths.

The method of making surface access points for the embedded microchannels in the method of the present invention can be understood by turning to FIG. 4, showing cross-sections of 6 structures labeled with letters "A" to "F", which were fabricated using the steps of the method of the present invention up to and including the step of annealing, the structures having two ridges and a spacing therebetween forming the trench. The spacings between the ridges for different structures in this figure have widths that progressively decrease from the structure "A" to the structure "F". This figure shows that as the ridges converge and the trench becomes smaller, the microchannels appearing in place of the initial trench after the step of annealing of the second optical material evolve from being open from the top, i.e. channels $28_a$, $28_b$, and $28_c$, to being partially closed, e.g. channels $28_d$ and $28_e$, to an almost closed channel $28_f$ which can be transformed into a completely enclosed embedded microchannel by performing additional high-temperature annealing.

Therefore, using the method of the present invention, an embedded microchannel having a surface access point, i.e. an opening in the upper surface of the waveguiding structure of the present invention, can be formed by simply increasing the width of the trench in a location in the structure where the opening is desired, typically at or near an end of the structure. Forming a trench having a widened portion at one or both ends thereof, for example the trench 28 in FIG. 1D, can easily be accomplished by using the mask 20 wherein the gap 24 widens towards one end thereof in a direction normal to the plane of the figure.

Figures 5A, 5B:
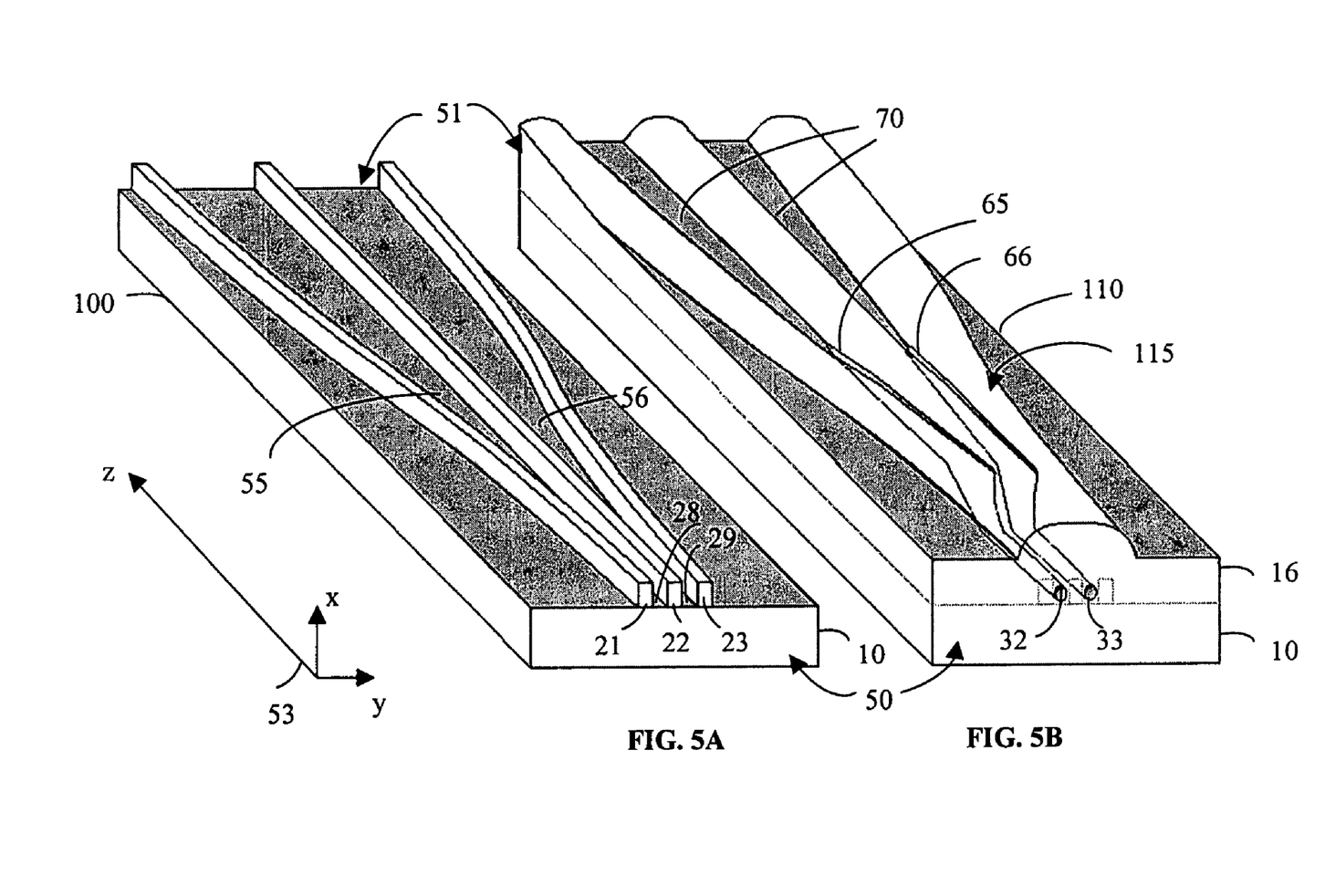
FIG. 5A is a diagram of a three-ridge template with divergent ridges.
FIG. 5B is a diagram of a waveguiding structure fabricated from the three-ridge template shown in FIG. 5A, having surface microchannel access opening.

By way of example, FIG. 5A shows a 3-dimensional view of a section 100 of the planar template described hereinabove with reference to FIG. 1D, having the three ridges 21, 22 and 23 extending from a first end 50 of the section 100 to a second end 51 thereof in a z direction of a reference Cartesian coordinate system (x,y,z) 53. The three ridges 21, 22 and 23 are closely spaced forming the narrow trenches 28 and 29 at the first end 50 of the template section 100, but diverge towards the second end 51 of the template 100, forming widened portions 55, 56 of the trenches. By performing the aforedescribed steps of depositing and subsequent annealing of the BPSG layer 16, a waveguiding section 110 shown in FIG. 5B is formed from the template section 100. At the first end 50 of this waveguiding section, the embedded microchannels 32, 33 are formed from the closely-space portions of the trenches 28, 29; these microchannels however change towards the second end 51 of the section as the trenches widen, first into partly open channels with openings 66, 65 in the upper surface 115 of the BPSG layer 16, and then into completely open valleys 70 at the second end 51 of the structure 110. As a result, inlets for the embedded microchannels 32, 33 are formed with the openings 65, 66, which provide surface, or in-plane access for the embedded microchannels. Additionally, in some embodiments the open areas 70 leading to the channels 32, 33 inlets can be expanded and shaped to form separate micro-cuvettes for holding a fluid for integration into the waveguiding structure 110. The fluid can then be easily delivered into the embedded microchannels by simply filling the micro-cuvettes 70 with the fluid and relying on the capillary forces to fill the microchannels 32, 33 with it. In other embodiments, the fluid can be delivered into the microchannels by injection under pressure.

Several exemplary embodiments, wherein the method of the present invention for fabricating waveguiding structures with embedded microchannels is applied for fabrication of novel types of microfluidic devices, will now be described with reference to FIGS. 6-9. In all these embodiments, fabrication of the device structures involves substantially the same processing steps described hereinabove with reference to FIGS. 1A-1F, but using different photolithographic masks 20 defining the ridge and trench locations. Therefore, in FIGS. 6-9, the device structures are illustrated via a top view of the mask used in fabrication of each of the structures. Simultaneously, these figures show a top view of the ridge templates fabricated using the respective masks, with the ridges represented by dark or patterned stripes, and with dashed lines showing locations of the embedded microchannels after the steps of depositing, and subsequent annealing of the second optical material over the ridge templates.

One type of microfluidic devices that can be fabricated using the method of the present invention includes devices based on evanescent field interaction between a fluid within the embedded microchannel and an optical mode propagating in the waveguiding structure of the device. In these types of devices, at least on of the ridges 21, 22 and 23 in FIGS. 1D-1F, for example—the first ridge 21, is dimensioned so that it forms a core of a ridge waveguide, while the layer 16 of the second optical material, and a top layer of the substrate 10 below the ridge 21, form two cladding layers of the ridge waveguide. The embedded microchannel 32 is incorporated in the cladding layer 16 close to the ridge waveguide core 21, and is optically coupled to the core via the evanescent field of the core-guided optical mode of the ridge waveguide. By delivering a fluid into the microchannel 32, light propagation characteristics of the waveguiding structure can be measurably affected. Based on this approach, microfluidic devices for controlling light, and optical sensors for measuring one or more characteristics of microscopic amounts of fluid can be fabricated.

Figure 6:
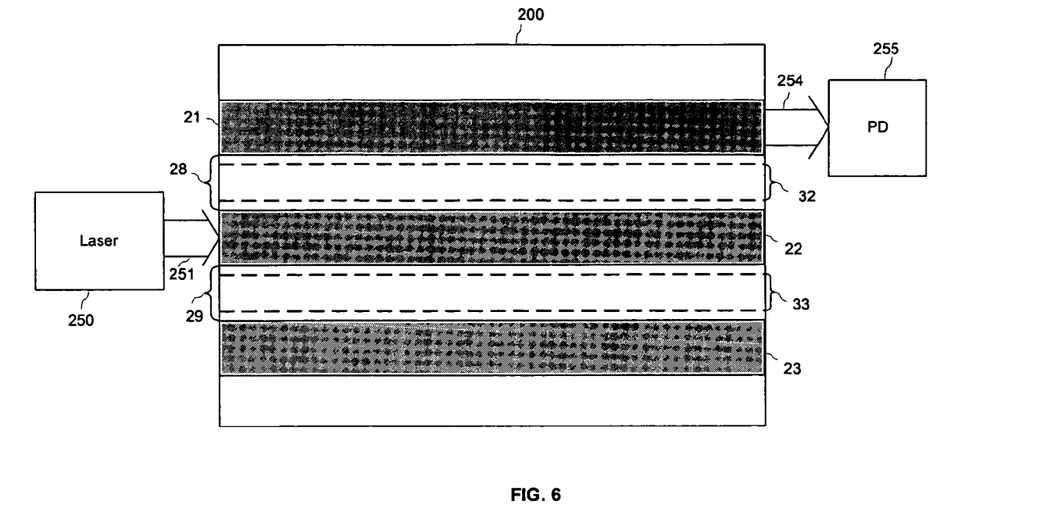
FIG. 6 is a diagram of a three-core microfluidic coupler.
Figure 7:
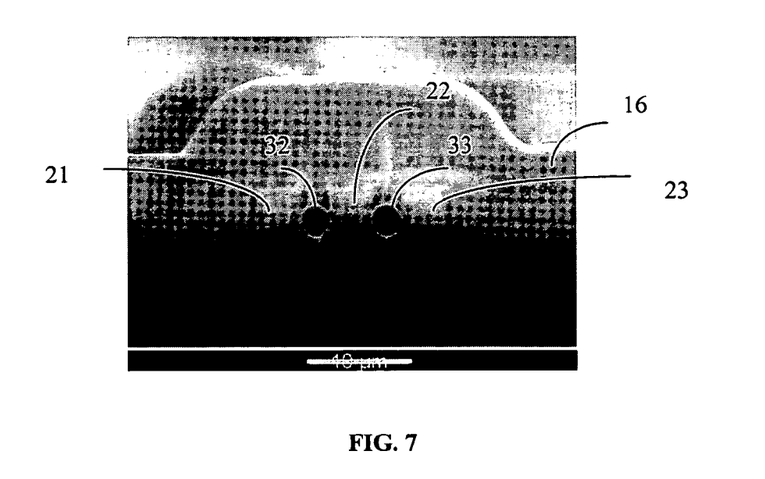
FIG. 7 is a cross-section of the three-core coupler structure with two embedded microchannels.

By way of example, FIG. 6 shows a three-ridge waveguiding structure 200, which is an embodiment of the waveguiding structure described hereinabove with reference to FIGS. 1A-1F, that can be used as an optical sensor for determining a refractive index of a liquid. Details of the fabrication and optical testing of the waveguiding structure 200 are given in an article entitled "*Silica-on-Silicon Optical Sensor Based on Integrated Waveguides and Microchannels*", published in Phot. Techn. Lett. No 17(2), p 441-443, 2005, which is authored by the inventors of the present invention, and is incorporated herein by reference, and in an article entitled "*Microchannels for the integration of liquid media in silica waveguide structures*", published in Technical Digest of Integrated Photonics Research and Applications, Paper IMD3, San Diego, Calif., Apr. 11-13, 2005, which is also authored by the inventors of the present invention, and is also incorporated herein by reference. In this embodiment, the germanium-doped silica ridges 21, 22 and 23 are 3.5 micrometers wide and 6.0 micrometers high, separated by 3.5 micrometers wide spacing 28, 29 wherein the quasi-circular channels 32 and 33, each approximately 3 micrometers in diameter, were formed. The ridges 21, 22 and 23 were patterned in the layer 15 of germanium-doped glass shown, e.g. in FIG. 1B, deposited over a top thermal oxide layer of a silicon wafer. An index step between the thermal oxide and the germanium-doped ridges 21, 22 and 23 is approximately $1.0 \times 10^{-2}$. The capping BPSG layer was then deposited over the ridges and annealed as described hereinabove, thereby forming, from the suitably dimesioned ridges 21, 22 and 23, three ridge waveguides having the ridges 21, 22 and 23 as their respective cores, and the BPSG layer 16 and the thermal oxide layer on the silicon wafer forming their claddings. The BPSG layer 16 was index matched to the thermal oxide layer. Two ridges 21, 22 and the spacing 28 therebetween are dimensioned so to form a two-core optical coupler having a coupling region in the spacing 28 incorporating the embedded microchannel 32, when the embedded microchannel 32 is filled with an index-matching liquid. Similarly, the ridges 22, 23 and the spacing 29 therebetween form another two-core optical coupler having the embedded microchannel 33 in a coupling region 29, when the embedded microchannel 33 is filled with an index-matching liquid. When the refractive index of both microchannels 32 and 33 is approximately matched to that of the cladding layer 16, the structure becomes a three-core directional coupler. For the particular structure parameters given hereinabove by way of example, the coupling length between waveguide pairs 21, 22 and 22, 23 is on the order of 100 micrometers at a wavelength of 1550 nm. FIG. 7 shows a photograph of a cross-sectional view of the waveguiding structure 200 fabricated as described hereinabove, with the microchannels 32, 33 clearly visible between the ridges 21, 22 and 23, capped with the BPSG layer 16.

The 3-micrometer channels 32, 33 can draw liquids through capillarity if one end of the device is dipped into a suitable liquid. Solvents such as ethanol are drawn quickly, at a speed greater than 200 micrometers per second, while thicker liquids such as index matching oils, having typical viscosity of about 16 cps, require a few minutes to be drawn over a distance of one centimeter. More viscous substances such as optical adhesives, which typically have about 300 cps viscosity, are drawn in at speeds on the order of 3 micrometers per second.

By coupling a laser beam 251 from a laser device 250 into one of the ridge waveguides 21, 22 and 23 at one end of the three-core optical coupler 200, e.g. into the central waveguide's core 22 as shown in FIG. 6, and measuring light output 254 using a sensing device 255 coupled to one of the ridges 21, 22 and 23 at the other end of the coupler 200, refractive index of the fluid within the microchannels 32, 33 can be optically sampled.

In another embodiment, the ridge template can include end portions having divergent ridges and widened trenches for forming surface inlet and outlet openings for the microchannels 32, 33 as described hereinabove with reference to FIGS. 5A,B.

The structure in FIGS. 6 and 7 can be used for refractive index based fluid sensing, or sampling, for a range of refractive indices of the fluid between 1.40 and 1.48, at a precision of about $10^{-4}$ for a base index of 1.44. In this refractive index range, the refractive indexes of the channels 32, 33 affect the power exchange between the rectangular cores 21, 22 and 23, effectively changing the coupling length.

Although the three-core design of the waveguiding structure 200, as opposed to a two-core version with a single embedded microchannel channel, is not essential to the sensing function, the redundant third waveguide could be used to increase an average sensitivity of the measurement by initially launching the light into one of the lateral waveguides 21 or 22. In our experiments, the channels were filled with a refractive index matching oil having the refractive index n~1.44 at 1550 nm, and the refractive index change was achieved through changing the temperature of the device.

Such a device enables the detection of substances present in the liquid medium within the microchannels, provided that their presence can induce a change in the refractive index of the liquid on the order of $10^{-4}$ for this particular device design. The sensitivity of the detection will be enhanced if a substance to be detected has an absorption peak near a probing wavelength. Also, specific chemical dyes can be used to enhance the detection sensitivity for a given substance. Measuring the refractive index at a number of probing wavelengths would allow the specificity of the detection to be established. The operating wavelength range of the device 200 shown in FIGS. 6 and 7 can be shifted to shorter wavelengths by scaling down the dimensions of the ridges 21, 22 and 23 and the trenches 28, 29 therebetween approximately proportionally to the wavelength reduction. Operation of the device 200 in the visible spectrum may thus be attained easily with about 1-micrometer feature sizes.

Another group of microfluidic devices that can be manufactured using the method of the present invention, includes devices based on liquid-core microchannel waveguides. These devices can be obtained using the waveguiding structures with embedded microchannels of the present invention, for example of the type shown in FIGS. 1F, 5B, 6, by filling the microchannels with fluids having a refractive index $n_f$ higher than the refractive index of a surrounding material, e.g. higher than at least one of the refractive indexes of the first optical material $n_1$, and the second optical material $n_2$.

Efficient coupling of light into a liquid-core waveguide may however present technical problems. Advantageously, the method of the present invention, wherein embedded microchannels and conventional ridge waveguides are co-fabricated within a single process using conventional lithographic and deposition technologies, enables also fabricating a junction of a conventional silica waveguide with the microchannel liquid-core waveguide within the same technological process, as described hereinbelow.

Figure 8A:
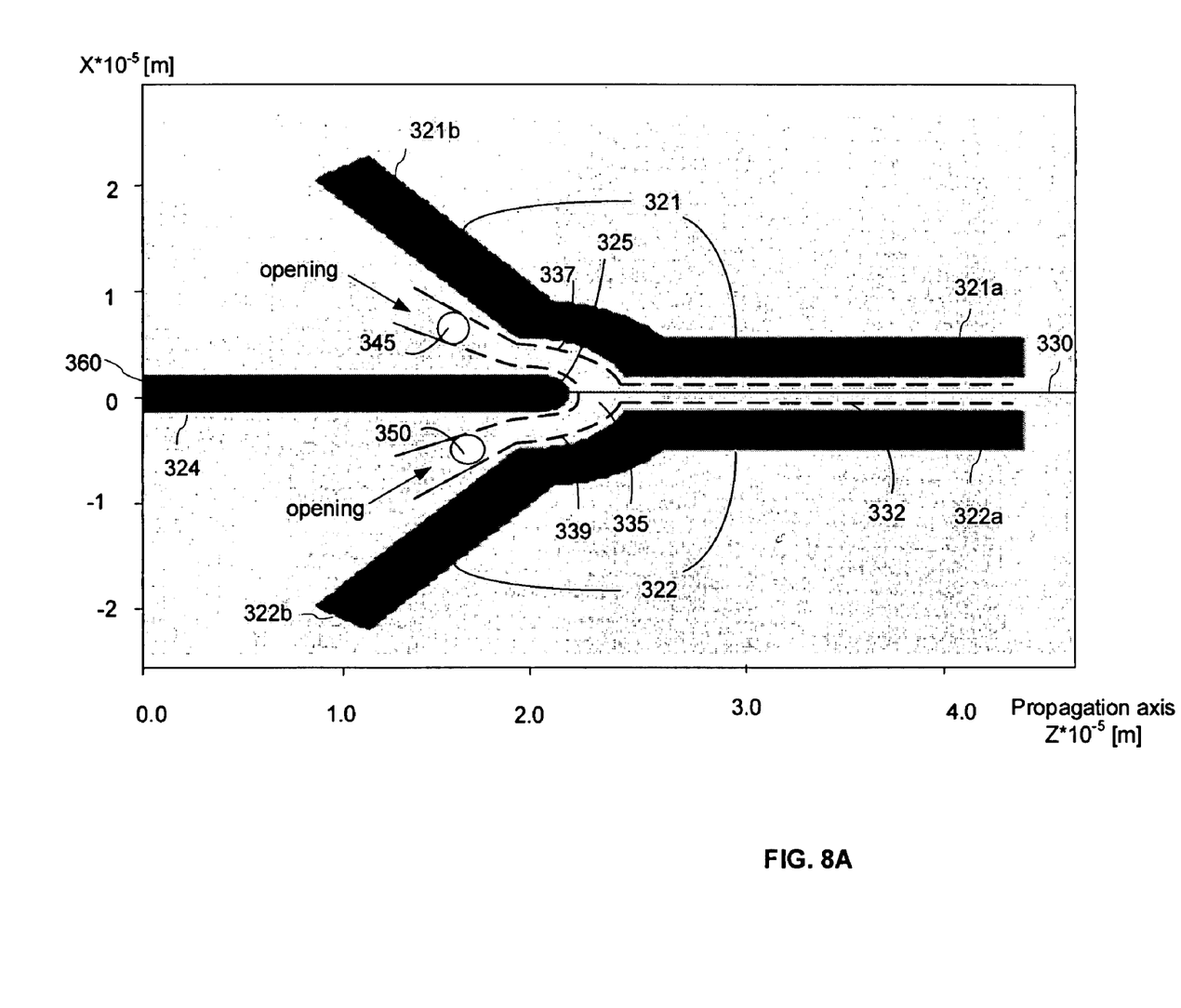
FIG. 8A is diagram representing a Y-shaped waveguide-microchannel junction device and a mask for the fabrication thereof.

With reference to FIG. 8A, a ridge template structure is formed using the method steps of the present invention described hereinabove with reference to FIGS. 1A-1D, i.e. by first depositing the germanium-doped silica layer as the first optical material 15 onto a silicon substrate, and then patterning said layer using a metal mask shown in FIG. 8A with black stripes, the black stripes simultaneously representing ridges formed after the step of patterning. The ridge template structure includes a first ridge 321 and a second ridge 322, said first and second ridges having parallel closely-spaced portions 321a and 322a respectively for forming a hollow embedded microchannel 332 therebetween, and divergent portions 321b, 322b. The ridges 321 and 322 have rectangular or trapezoid cross-section, and their parallel portions 321a, 322a form the indented feature 25 of FIG. 1D having a narrow trench in the middle for forming the hollow microchannel 332 therein after depositing the second optical material 16, e.g. the BPSG capping layer. Comparing to the structures described hereinabove with references to FIGS. 1D-1F, 5A, 5B, 6 and 7, the ridge structure of the embodiment shown in FIG. 8A does not have a third ridge parallel to the parallel portions of the first and second ridges 321, 322 for forming a second embedded microchannel. Instead, it includes an additional germanium-doped silica ridge 324, which has a rectangular or trapezoidal cross-section dimensioned for forming a core of an optical waveguide at the operating wavelength $\lambda$ after the PECVD deposition of the BPSG cladding layer. The ridge 324, which is also referred to hereinafter as a forth ridge, has an end portion 325, which is positioned along an optical path 330 between the divergent portions 321b, 322b of the first and second waveguides, and aligned with the trench formed between the ridge portions 321a, 322a, or at least with a straight portion of said trench aligned along the optical path 330 and facing the end portion of the ridge 324.

After the steps of depositing and re-flowing of the second optical material, e.g. the BPSG, over the ridge structure, the second optical material selected so that it has a refractive index lower than the refractive index of the germanium-doped silica ridge 324, an access ridge waveguide is formed from the ridge 324, the ridge 324 becoming the core of the access waveguide, said access waveguide aligned and butt-coupled with a straight portion of the embedded microchannel 332 for coupling light into the embedded microchannel 332. The access waveguide 324 will also be referred hereinafter as a first access waveguide.

Simultaneously, two microchannel inlet portions 337, 339 with openings 345, 350 in the upper surface of the BPSG layer are formed between the end portion 325 of the forth ridge 324 and the divergent portions 321b, 322b of the first and second ridges, similarly as described hereinabove with reference to FIGS. 4, 5A, 5B. These microchannel inlets can be used as means for delivering sample material, e.g. a fluid, in the microchannel 332, thereby forming from said embedded microchannel a liquid-core microchannel waveguide, depending on the fluid refractive index. The means for delivering sample material can include, optionally, micro-cuvettes that can be formed between the ridges 321b and 324, and 322b and 324 for holding the liquid. Advantageously, the microchannel inlet portions 337, 339 formed by the method of present invention are funnel shaped and inclined, or ramped, downwards from the approximately elliptical or circular openings 345, 350 in the upper surface of the structure downwards towards the embedded microchannel to provide for a gradual introduction of fluid into the microchannel to ensure laminar flow.

The resulting structure shown in FIG. 8A can be used as an integrated waveguide-microchannel junction, which enables launching of light into the liquid-core microchannel waveguide 332 via the access waveguide 324 without resorting to coupling light into the microchannel endpoint on an edge facet of the structure, thus obviating potential negative effects of a shape and position of the fluid's meniscus at that edge facet on coupling of the light into the microchannel. Advantageously, the inlet channels 337, 339 with surface access points 345, and, 350, enable volatile liquids to be used within the microchannels, with the optical coupling of light into the liquid-filled microchannel being unaffected by the liquid's evaporation. By coupling light into the embedded microchannel 332 through the first access waveguide 324, and delivering a fluid into the embedded microchannel, one or more characteristics of the light coupled into the microchannel can be changed, e.g. the light phase, intensity or polarization, by the light-fluid interaction. The waveguide-microchannel junction shown in FIG. 8A can be thus used in a variety of light controlling devices.

In some embodiments, the ridges 321, 322 can be dimensioned to form additional waveguide cores, thereby providing a three-core waveguiding structure, for example—a three core coupler, wherein the central core is formed by a liquid within the embedded microchannel 332 and is sandwiched between two silica ridge cores 321a, 322a. In other embodiments, the ridges 321, 322 are used mainly for forming the microchannels 332 in the trench therebetween, and can be arbitrary wide, and/or index-matched to the capping layer of the second optical material.

Figure 8B:
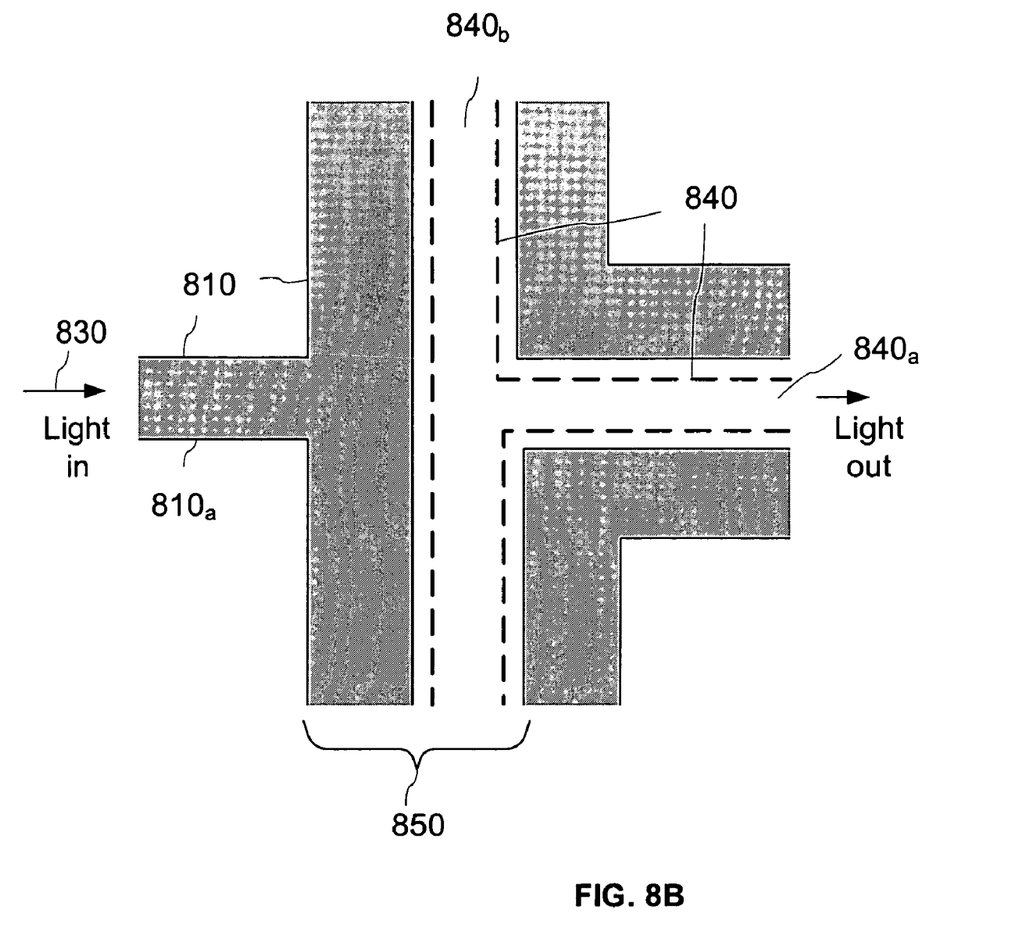
FIG. 8B is diagram representing a T-shaped waveguide-microchannel junction and a mask for the fabrication thereof.

FIG. 8B shows another embodiment of the waveguide-microchannel junction that can be fabricated by the method of the present invention. In this embodiment, a T-shaped embedded microchannel 840 has a portion 840a which is aligned with an end portion 810a of the forth ridge 810, which is also T-shaped. After the steps of depositing and annealing of the second optical material over the ridge structure shown in FIG. 8B by the diagonal-patterned stripes, an access waveguide is formed from the end portion 810a of the ridge 810, said end portion is aligned with the embedded microchannel portion 840a. In this structure, light 830 coupled into the ridge core 810a of the access waveguide, is then coupled into the portion 840a of the microchannel 840 via a "free-space" transition area 850.

Figure 9:
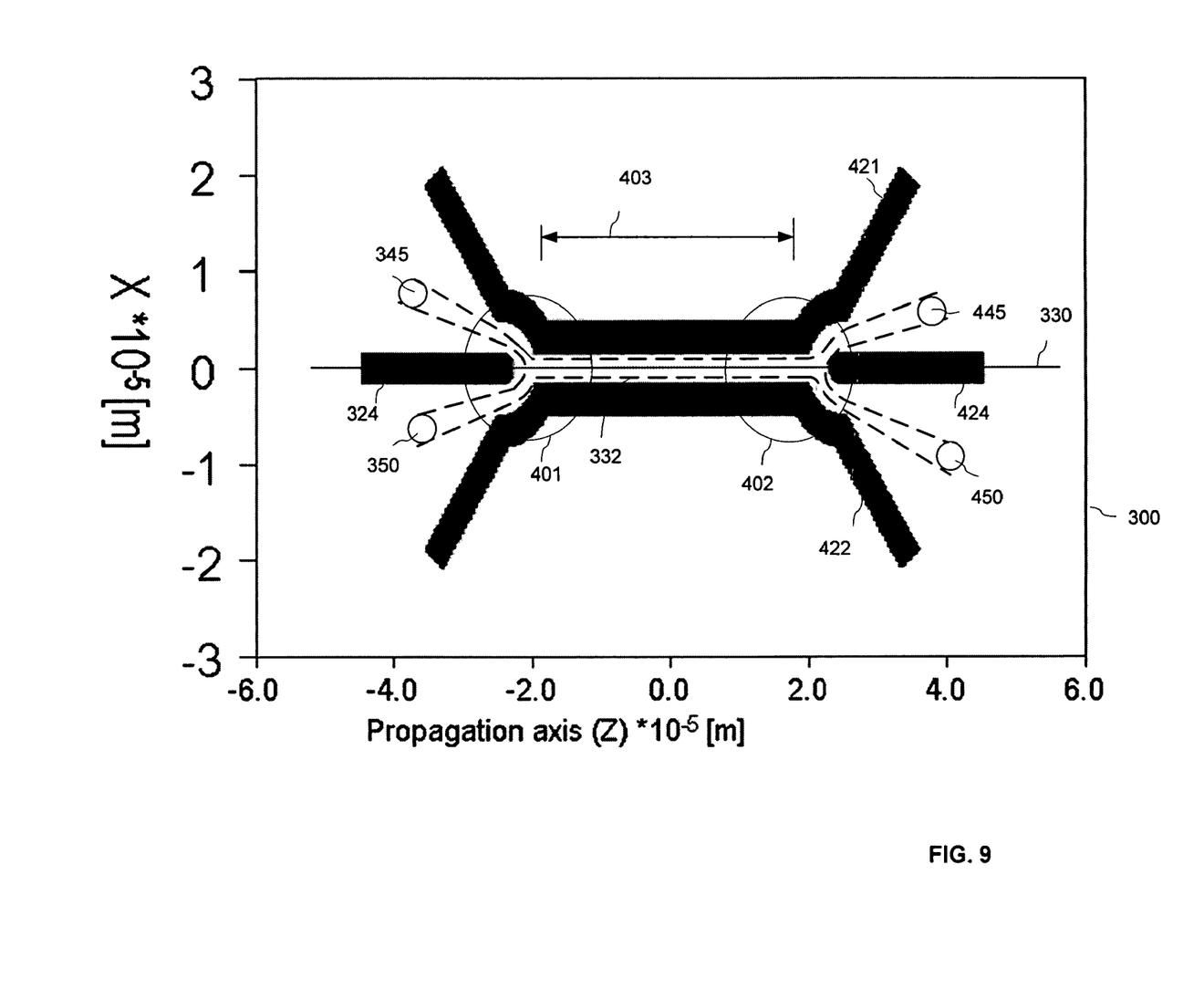
FIG. 9 is diagram representing a liquid-core microchannel waveguide device with two waveguide-microchannel junctions.

FIG. 9 schematically shows an integrated microchannel waveguide device 300 which is formed by concatenating two waveguide-microchannel junction structures shown in FIG. 8, i.e. by forming a second access waveguide 424 providing a second waveguide-microchannel junction 402 at an end portion of the embedded microchannel 332 opposing to the first access waveguide 324 and the first waveguide-microchannel junction 401, for coupling light out of the microchannel 332. Similar to FIG. 8, the black stripes 324, 421, 422, and 424 in FIG. 8 represent simultaneously a mask used in the patterning step of the fabrication method of the present invention for this structure, and the silica ridges formed as a result of the patterning step.

Using the two concatenated junctions 401, 402, a liquid-core waveguide section 403 with variable optical properties can be integrated into silica-waveguide based optical devices using the access ridge waveguides 324, 424 as input and output optical ports. Optical properties of the waveguide section 403 are determined by the nature of the liquid inserted into the channel. The liquid portion of the microchannel 332 may be connected to a microfluidic pump or a circulation system via one of the surface access openings 345, 350 at one end of the channel, and one of the openings 445, 450 at the other end of the channel 332. A change in the optical properties of the substance flowing discretely or continuously in the channel 332 produces a change in the optical properties of the liquid-core waveguide, thereby enabling the device 300 to be used as a waveguide section with controllable optical properties.

In other embodiments, passive or active optical properties of the liquid media delivered into the microchannel 332 may directly be exploited in a integrated optics environment, for applications in spectroscopy, substance detection, nonlinear optics, all-optical switching and microfluid-driven optical switching. For example, an optical phase of a light beam passed through the liquid-filled microchannel 332 may be modified either though a change in composition of the liquid, or by environmental changes affecting the optical properties of the liquid. Phase changes of the output light may be detected using either an external or integrated interferometer, for example a Mach-Zehnder interferometer structure with the device 300 placed within one of the arms of the interferometer. The output of the interferometer then can be modulated through a phase change in the device described here. Alternatively or additionally, an optical transmission coefficient of the device 300 may be modified by a change in composition of the liquid contained in the channel section 332, either by changing the liquid's absorption coefficient or altering the waveguiding properties of the channel section 332 with a change in refractive index of the liquid therein. In other embodiments, changes in concentration of a fluorescent component within the liquid can be identified by observing the amount of fluorescence at the surface of the device 300 or from the liquid existing the device.

Yet in other embodiments, the fluid is delivered into the microchannel 332 containing optically active material and/or nonlinear optical material, for forming liquid-core waveguide devices for controlling, modifying or generating light. For example, the liquid conveyed into the microchannel 332 can contain quantum dot material, i.e. sub-micron sized grains of semiconductor or other material, e.g. silicon, which are known to possess optical properties, e.g. optical nonlinearity and ability to provide optical gain when pumped, superior to the optical properties of conventional bulk materials.

In some embodiments, the first and second access waveguides 324 and 424 incorporate first and second optical reflectors respectively, said optical reflectors not shown in FIG. 9, for example waveguide Bragg gratings well known in the art, for forming a waveguide cavity comprising the microchannel 332 at the operating wavelength $\lambda$. This cavity can be used for enhancing useful effects of the liquid within the microchannel 332 on the light propagating therethrough.

In another embodiment, this cavity can be used for forming a microfluidic laser; in such a laser, an optically-active fluid, or a fluid containing optically-active materials such as the quantum dots, is delivered into the embedded microchannel 332, the optically active material exhibiting optical gain at the operating wavelength $\lambda$ in response to optical pumping at a pump wavelength $\lambda_p$. The fluid-filled microchannel 332 is then optically pumped via e.g. the first access waveguide 324 at the pump wavelength $\lambda_p$ so to excite the laser action within the microfluidic waveguide cavity including the fluid-filled microchannel 332. As those skilled in the art would appreciate, in this embodiment the first optical reflector formed within the first access waveguide 324 or at an end thereof, is preferably substantially reflective at the operating wavelength $\lambda$ and substantially transmissive at the pump wavelength $\lambda_p$.

In addition to microfluidic applications of the present invention described hereinabove, the method of the present invention can be used in many other embodiments and for various other applications. For example, the hollow or air-filled microchannels of the present invention inserted in a silica structure may enable index-guiding effects from the air/silica interfaces, and the use of microchannels as hollow waveguides. In germanium-doped ridge waveguides, the lateral index step may be modified by the presence of the air channel nearby, enabling control of the waveguides via e.g. an induced birefringence, and higher bending radii in the plane of the substrate via a higher lateral index step; the microchannels of the present invention affect guiding properties of the adjacent ridge waveguides similarly to air trenches, but are buried within the structure, which protects the air/silica interface from external contamination.

Figure 10:
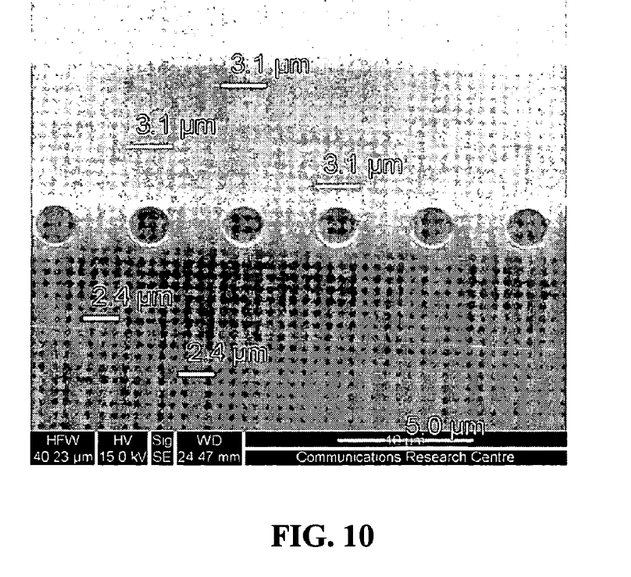
FIG. 10 is a photograph of a cross-section of a waveguiding structure incorporating a one-dimensional microchannel array; and, FIG. 11 is a photograph of a cross-section of a waveguiding structure incorporating a two-dimensional microchannel array.
Figure 11:
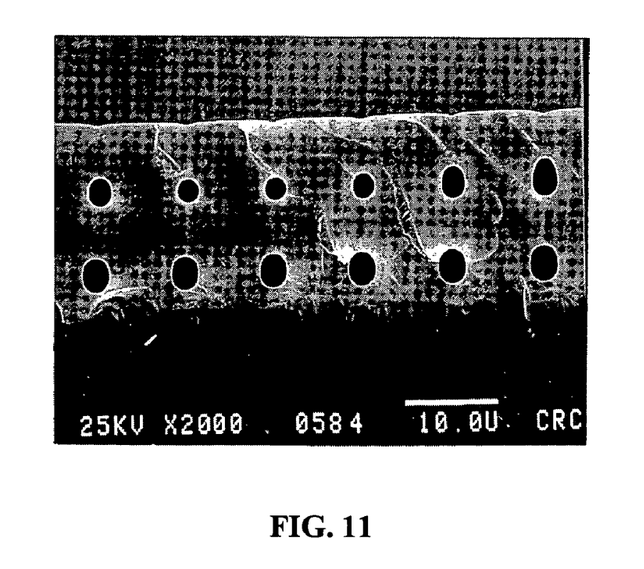

In other embodiments of the invention, one-dimensional (1D) and two-dimensional (2D) arrays of microchannels can be fabricated using the method of the present invention. The 1D microchannel arrays are provided by patterning the first optical materials with a plurality of closely spaced ridges forming a plurality of trenches therebetween, and then performing the steps of depositing and annealing of the second optical material. An example of such 1D array of hollow embedded microchannels fabricated in a BPSG layer between germanium-doped ridges by the method of the present invention is shown in FIG. 10. In other embodiments, multi-layer structures may be fabricated by patterning a new ridge template over the upper layer of the second optical material, and repeating the deposition and annealing process. The new ridge template can be patterned within the second optical material wherein the first microchannel array is formed. Alternatively, one or more additional layers can be first deposited over the first layer of the second optical material capping the first before the step of patterning of the new ridge template. These steps can be repeated for forming a multi-layer waveguiding structure comprising a two-dimensional array of the embedded microchannels. An example of the 2D array of embedded hollow microchannels fabricated using the method of the present invention is shown in FIG. 11. Further details of fabrication of the microchannel arrays and examples of waveguiding structures incorporating the ararys are given in an article entitled "*Fabrication of microchannels integrated with silica waveguides*", published in Technical Digest of Integrated Photonics Research and Applications, Paper IMD4, San Diego, Calif., Apr. 11-13, 2005, which is authored by the inventors of the present invention, and is incorporated herein by reference.

Advantageously, the method of the present invention enables tightly controlled formation of the individual microchannels, groups of microchannels and 1D and 2D microchannel arrays in the glass supporting material. The composition and properties of the various glass layers can be adjusted to optimize carious characteristics of the template and forming of the voids, and optical properties of the whole waveguiding structure can be tailored to a particular application. Manipulation of the properties of specific ridge waveguides can be achieved by tailoring the layer compositions and refractive indices, and by creating voids in close proximity to waveguide cores. The method enables to controllably vary the microchannel diameter, spacing and shape in fabricated structures; circular holes or elliptical "slots" can be reproducibly formed by adjusting the template geometry, the film thicknesses and the annealing conditions. Regular 2D arrays of the microchannels can be fabricated using the method of the present invention by carefully aligned photolithographic patterning of subsequent template layers, wherein the microchannel diameter and/or the array period h is dimensioned for forming a photonic crystal structure having a photonic bandgap at the operating wavelength $\lambda$, e.g. by dimensioning the microchannel array so the $h=\lambda/2$. The method enables fabrication of the photonic crystals, or photonic band gap materials wherein the hollow microchannels are oriented in-plane with the substrate, as opposed to more conventional photonic bandgap materials fabricated by forming holes in a substrate in a direction perpendicular thereto.

The aforedescribed embodiments of the method and waveguiding structure of the present invention are not meant to limit the scope of the invention, but merely provide examples of making and using of the invention in some of it aspects. It should be understood also that each of the preceding embodiments of the present invention may utilize a portion of another embodiment.

Of course numerous other embodiments may be envisioned without departing from the spirit and scope of the invention.

We claim:

1. A method for fabricating an optical waveguiding structure comprising the steps of:
   a) forming on a planar substrate a first ridge with a trench adjacent thereto with a first optical material,
   b) depositing a second optical material over the first ridge and the trench so that an at least partially capped channel is formed from at least a portion of the trench; and,
   c) re-flowing the second optical material by thermal annealing to form an embedded microchannel from said at least partially capped channel,
   wherein the first ridge and the embedded microchannel cooperate to form the optical waveguiding structure having a waveguiding direction collinear with the embedded microchannel.

2. A method according to claim 1, wherein step (a) comprises forming the trench with a widened portion at one end thereof, and wherein in step (c) an inlet for the embedded microchannel forms from said widened portion, said inlet having an opening in an upper surface of the second optical material for providing an in-plane access to the embedded microchannel.

3. A method according to claim 2, further comprising the step of conveying a fluid into the embedded microchannel through the inlet for forming a liquid-core microchannel waveguide, the fluid having a refractive index higher than a refractive index of at least one of the first material and the second material.

4. A method of claim 1, wherein step (a) comprises forming the trench between the first ridge and a second ridge of the first optical material.

5. A method of claim 4, wherein step (c) comprises forming two ridge waveguides from the first and second ridges having the embedded microchannel in a spacing therebetween, the first and second ridges and the spacing therebetween dimensioned to form a two-core optical coupler having a coupling region comprising the embedded microchannel.

6. A method of claim 5 further comprising:
   delivering a fluid into the microchannel,
   coupling a laser beam into one of the two ridge waveguides at one end of the two-core optical coupler, and
   optically sampling the fluid using a sensing device coupled to one of the ridges at the other end of said two-core optical coupler.

7. A method according to claim 4, wherein step (a) comprises forming a third ridge adjacent to the second ridge and separated therefrom by a second trench, and wherein step (c) comprises forming a three-core optical coupler having two coupling regions optically coupling adjacent cores of the three-core coupler, the two coupling regions comprising embedded microchannels.

8. A method of claim 7 further comprising:
   delivering a fluid into at least one of the embedded microchannels,
   coupling a laser beam into one of the cores at one end of the three-core optical coupler, and
   optically sampling the fluid using a sensing device coupled to one of the cores at the other end of said three-core coupler.

9. A method according to claim 1, wherein:
   step (a) includes forming a fourth ridge from the first optical material, said fourth ridge having an end portion aligned with a portion of the trench, and
   step (c) includes forming, from said fourth ridge, a first access waveguide aligned with a portion of the embedded microchannel and optically coupled thereto, thereby forming a first waveguide-microchannel junction.

10. A method according to claim 9, further comprising the steps of:
    coupling light into the embedded microchannel through the first access waveguide, and
    delivering a fluid into the embedded microchannel for changing a characteristic of the light coupled into the microchannel.

11. A method according to claim 10, wherein the fluid comprises one of optically active material and nonlinear optical material.

12. A method according to claim 9, wherein the embedded microchannel has an end portion opposing the first waveguide-microchannel junction, and wherein step c) includes forming a second access waveguide providing a second waveguide-microchannel junction at the opposing end portion of the embedded microchannel for coupling light out of the microchannel.

13. A method according to claim 12, further comprising forming optical reflectors in the first and second access waveguides for forming a waveguide cavity comprising the embedded microchannel.

14. A method according to claim 13, further comprising delivering a fluid comprising optically active material into the embedded microchannel for forming a microfluidic laser.

15. A method according to claim 1, wherein step (a) comprises depositing a layer of first optical material on the planar substrate, patterning said layer with a mask, and etching said layer to remove portions thereof for forming the first ridge with the trench adjacent thereto.

16. A method according to claim 1, wherein the first optical material comprises at least one material selected from the group consisting of silicon, silica, and doped silica.

17. A method according to claim 1, wherein the second optical material comprises doped silica having a melting temperature lower than a melting temperature of the first optical material.

18. A method according to claim 1, wherein the second optical material comprises borophosphosilicate (BPSG) glass.

19. A method according to claim 1, wherein step (a) comprises forming a plurality of trenches, so that a plurality of embedded microchannels is formed in step (c).

20. A method according to claim 19, further comprising repeating steps (a)-(c) to form a waveguiding structure comprising a two-dimensional array of embedded microchannels.

21. A method according to claim 20, wherein the two-dimensional array of embedded microchannels forms a photonic crystal.

* * * * *